United States Patent [19]

Bush

[11] Patent Number: 5,139,506
[45] Date of Patent: Aug. 18, 1992

[54] VALVULOTOME

[75] Inventor: Ronald G. Bush, Fort Washington, Pa.

[73] Assignee: Pilling Co., Fort Washington, Pa.

[21] Appl. No.: 673,331

[22] Filed: Mar. 22, 1991

[51] Int. Cl.$^5$ .............................................. A61B 17/32
[52] U.S. Cl. ...................................................... 606/159
[58] Field of Search ....................... 606/159, 170, 160;
604/22; 128/751

[56] References Cited

U.S. PATENT DOCUMENTS

| 3,837,345 | 9/1974 | Matar | 606/159 |
| 4,952,215 | 8/1990 | Ouriel et al. | 606/159 |
| 5,047,041 | 9/1991 | Samuels | 606/159 |

Primary Examiner—Michael H. Thaler
Attorney, Agent, or Firm—Howson & Howson

[57] ABSTRACT

A valvulotome for surgically removing venous valves in order to convert a vein into an arterial bypass, comprises a thin, elongated rod capable of insertion into a vein and a head having a blunt tip secured to the distal end of the rod. The head has two sharp-pointed blades extending in the proximal direction from the proximal side of the tip. The point of each blade is located radially inwardly with respect to the outer surface of the tip, and each blade is defined by a pair of surfaces which are respectively parts of intersecting right, circular, cones, both coaxial with the rod but having different apex angles, and by a pair of surfaces lying in planes intersecting each other on a line peripendicular to and intersecting the axis of the rod. The planes and conical surfaces all intersect at the point of the blade. The blades are diametrically opposed, on opposite sides of the rod, the two planes and two conical surfaces defining one blade are the same as the two planes and two conical surfaces defining the other blade. The blades are formed by machining the conical surfaces on the proximal side of the tip, and forming the planar surfaces by two passes of a bevelled grinding wheel.

14 Claims, 2 Drawing Sheets

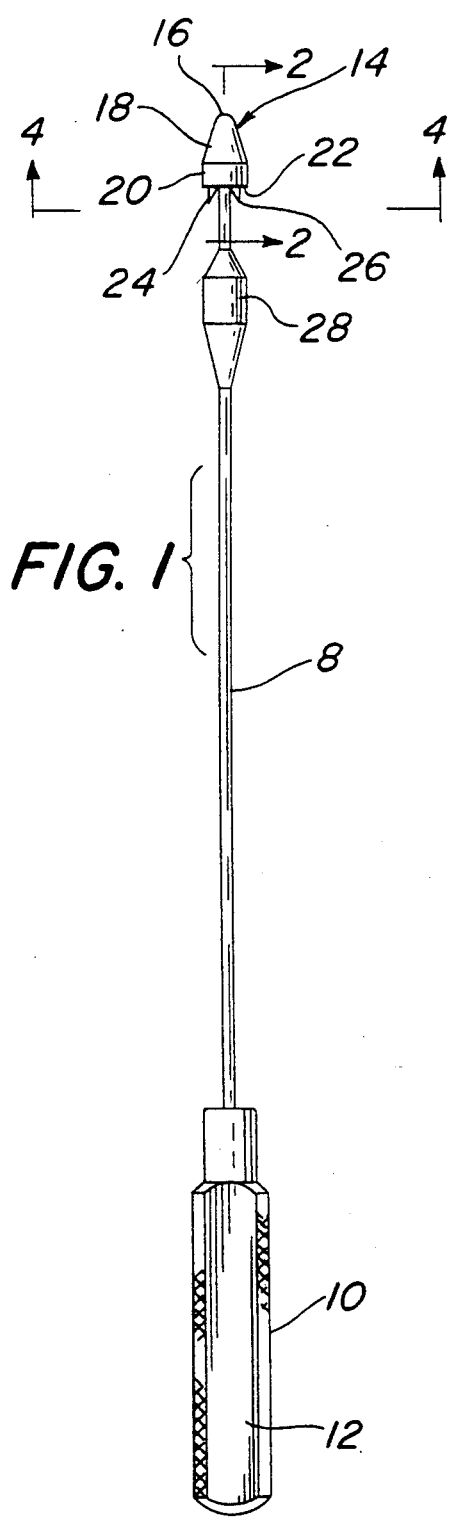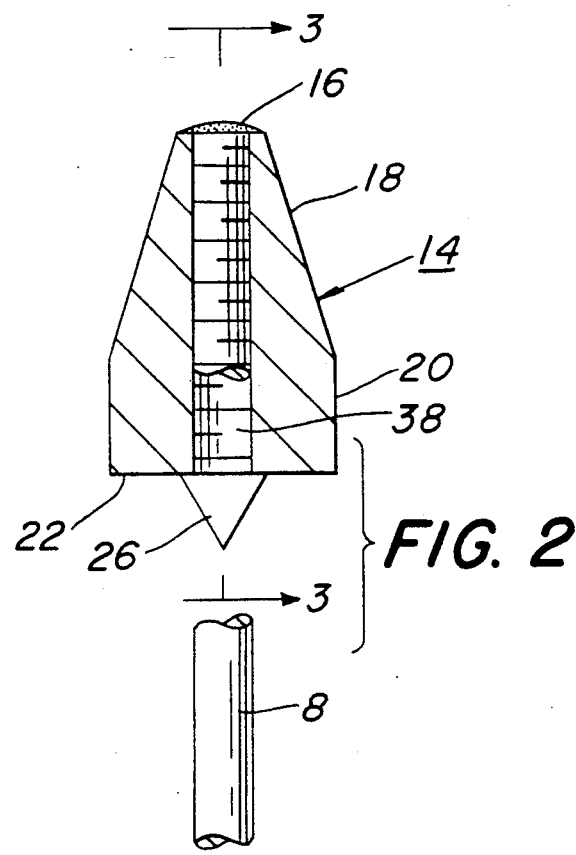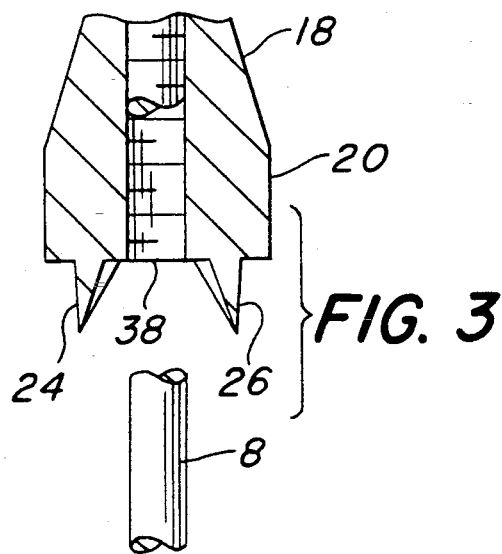

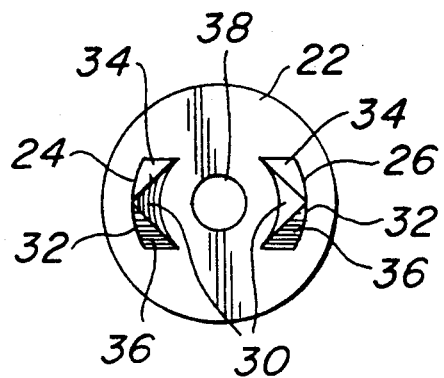
FIG. 4
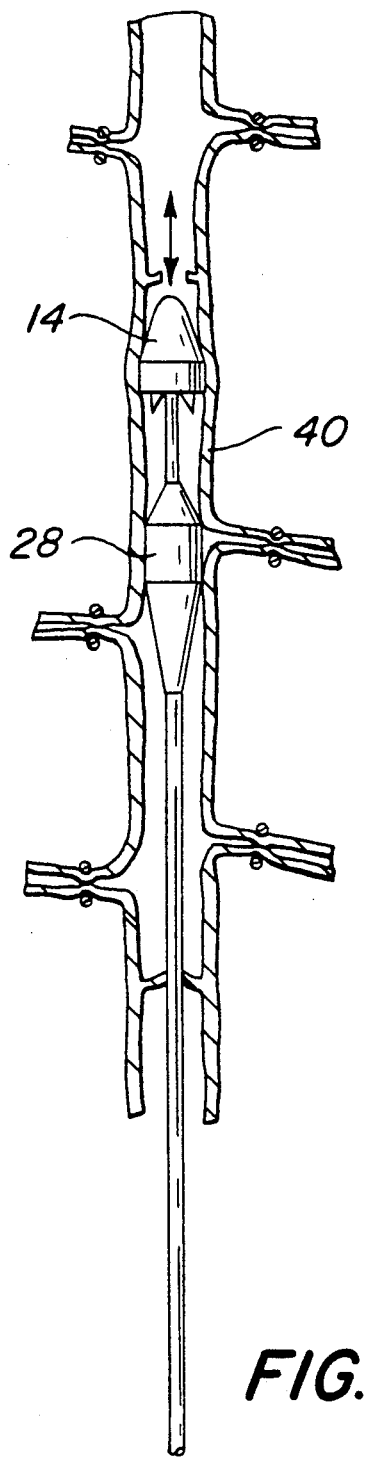
FIG. 5
FIG. 6

VALVULOTOME

BRIEF SUMMARY OF THE INVENTION

This invention pertains to valvulotomes for use in surgery, and in particular to an improved valvulotome adapted for cutting valve leaflets in a vein in order to make the vein usable as a by-pass vessel for an artery.

The invention is particularly adapted for in situ vein grafting, a surgical procedure used in the treatment of femoro-popliteal and distal arterial occlusive disease, a condition in which an artery in the patient's leg is blocked. In situ vein grafting is an operation in which a vein, typically but not necessarily the saphenous vein in the patient's leg, is modified to permit it to conduct blood in a direction opposite to the usual direction so that, when grafted to an occluded artery, it can serve as a by-pass vessel. In the modification of the vein, its side branches are closed off by ligation, and the one-way valves, several of which exist along the vein, are rendered inoperative by means of a valvulotome, which is used to cut the valve leaflets so that they can no longer prevent blood flow in directions opposite to the normal flow of blood toward the heart.

It is important in carrying out the procedure to destroy all of the valves in the by-pass vessel completely. Incomplete destruction of these valves may result in thrombus formation. Therefore, efforts have been made in the past to achieve reliable and complete destruction of the venous valves by valvulotomes of varying designs.

A typical valvulotome is the so-called "Mills retrograde valvulotome", which consists of an elongated rod having an L-shaped distal end with a bulbous tip and a blade, located between the bulbous tip and the elongated portion of the rod and facing in the proximal direction. The distal end of the valvulotome is passed through a valve and the instrument is then pulled in the reverse direction, causing the blade to cut through a valve leaflet. With this instrument, two or more passes are necessary for each valve to insure that both valve leaflets are sufficiently destroyed to permit arterial flow of blood.

Various instruments have been developed for the same purpose, as shown by patents such as U.S. Pat. No. 3,837,345 to Matar, U.S. Pat. No. 4,493,321 to Leather, and U.S. Pat. No. 4,655,217 to Reed. In general, these instruments, while having some advantages over the simpler retrograde valvulotome described above, are structurally more complex. Some are more difficult to use than the simpler retrograde valvulotome. Another problem with prior art valvulotomes, due to the fact that their cutting parts are extremely small in size, is that they are difficult to manufacture with accuracy and consistency.

The principal object of this invention is to provide a valvulotome which is simple to manufacture, which has blades of uniform high quality, and which is reliable, effective and easy to use in surgery.

The valvulotome in accordance with the invention, utilizes a thin, elongated rod capable of insertion into a vein. A head having a blunt tip is secured to the distal end of the rod. The head has at least one, and preferably two, sharp-pointed blades extending in the proximal direction from the proximal side of the tip. The point of each blade is located radially inwardly with respect to the outer surface of the tip, and each blade is defined by a pair of surfaces which are respectively parts of intersecting right, circular cones both coaxial with the rod but having different apex angles, and by a pair of surfaces which are respectively parts of two planes intersecting each other on a line perpendicular to and intersecting the axis of the rod. The planar surfaces and conical surfaces all intersect at the point of the blade. In the preferred form of the invention, the blades are diametrically opposed, on opposite sides of the rod, the two planar surfaces and two conical surfaces defining one blade are the same as the two planes and two conical surfaces defining the other blade. The blades can be formed simply by machining frusto-conical surfaces on the proximal side of the tip, and forming the planar surfaces by two passes of a bevelled grinding wheel.

Further objectives and advantages of the invention will be apparent from the following detailed description when read in conjunction with the drawings.

BRIEF DESCRIPTION OF THE DRAWINGS

FIG. 1 is a fragmentary elevational view of a valvulotome in accordance with a preferred embodiment of the invention;

FIG. 2 is a sectional view taken on plane 2—2 of FIG. 1;

FIG. 3 is a sectional view taken on plane 3—3 of FIG. 2;

FIG. 4 is a sectional view showing the proximal side of the tip of the valvulotome, taken on plane 4—4 of FIG. 1;

FIG. 5 is a perspective view of the tip; and

FIG. 6 is a sectional view of a vein, showing the valvulotome in use.

DETAILED DESCRIPTION

As shown in FIG. 1, the valvulotome comprises an elongated rod 8, typically of stainless steel, about 40 cm. in length and about 0.065 cm. in diameter. The length of the rod may be as high as 95 cm. or even longer, depending on the particular type of surgery in which the instrument is to be used. A knurled handle 10, affixed to the proximal end of the rod has a milled flat 12 to enable the surgeon to align the cutting blades of the valvulotome head to the valve leaflets. The line at which the edges of the valve cusps meet when the valve is closed is normally parallel to the surface of the adjacent skin. Thus, the surgeon can align the cutting blades with the valve leaflets simply by maintaining the milled flat 12 in a plane perpendicular to the skin adjacent to the approximate location of the valvulotome head.

As shown in FIGS. 1, 2 and 3, head 14 is a stainless steel element having a blunt tip 16, a tapered front portion 18 and a cylindrical rear portion 20, all designed to facilitate movement of the head through a vein. The rear portion 20 of the head is typically about 0.3 cm. in diameter, although valvulotomes can be provided with heads of various sizes to accommodate different vein dimensions, which depend on the patient and on the particular vein involved. The proximal face 22 of the head 14 is a plane perpendicular to the axis of rod 8, and has formed on it a pair of sharp-pointed blades 24 and 26 located in diametrically opposed relationship to each other on opposite sides of the rod and extending in the proximal direction. The points of the blades are located radially inward with respect to rear portion 20 of the head, and the head causes the wall of the vein to expand in the vicinity of the blades to protect the vein from being damaged by the blades.

Rod 8 has a dilator 28 spaced a short distance below head 14. This dilator, which is tapered at both ends, allows the valve leaflets in the vein to approach each other closely when cutting takes place while protecting the walls of the vein and the branch openings from being damaged by blades 24 and 26. The dilator preferably has the same diameter as the head. The length of the short section of rod 8 extending between the head and the dilator depends on the diameter of the head. The length of this section, measured along the axis of rod 8 from the location of the blade tips to the tip of the upper cone of the dilator, ranges from 1.5 mm. for a 2 mm. diameter head to 3.0 mm. for a 4 mm. head.

As shown in FIG. 4, each of blades 24 and 26 is partially defined by an inner surface 30, which is part of a cone and an outer surface 32 which is part of a cylinder. The apex angle of surface 30 is preferably approximately 60 degrees. The outer surface 32 may be thought of as a conical surface, as a cylinder is a species of a cone having a zero degree apex angle. In some cases it may be desirable to form the blades with a conically tapered outer surface, e.g. a surface tapered toward the proximal direction.

The blades are further defined by planar surfaces 34 and 36. These surfaces are inclined relative to the rod axis, and lie in planes which intersect each other, at an angle of approximately 60 degrees, along a line which passes perpendicularly through the axis of rod 8. As shown in FIG. 4, the four surfaces which define each blade intersect to form a sharp point. The blade configuration formed by these surfaces is highly effective for cutting venous valve leaflets.

Formation of the head 14 is carried out by first machining the head to form outer surfaces 18 and 20 and conical frusta in which surfaces 20 and 32 lie. A bore 38 (FIG. 3) is drilled in the head and threaded. The head is then hardened by heat treating.

Following heat treating, the blades are completed by grinding away portions of the conical frusta, using a grinding wheel having a 120 degree bevelled grinding surface. With the head secured in a jig, surface 34 is formed on both blades in a single pass of the grinding wheel. Then, the head is rotated 180 degrees, and surfaces 36 are formed by a second pass of the wheel. In this way, it is possible to form the blades with an extremely high degree of accuracy and consistency, with only two passes of the grinding wheel.

Following grinding, the head is electropolished. The dilator 28, which has a hollow lengthwise bore, is fitted over rod 8 and cemented in place. Rod 8 is then threaded into bore 38 in the head. The rod is rotated so that flat 12 (FIG. 1) is in a specific relationship to blades 24 and 26, and solder is then applied at tip 16, as shown in FIG. 2, to secure the head on the rod. Finally, the tip is polished smooth by a polishing wheel.

In surgery, assuming the great saphenous vein is to be used as an arterial by-pass, an incision is made to expose the vein, and the major vein branches are ligated flush to the vein. The valvulotome is introduced from the below, passed upwardly into the vein, rotated so that its blades are properly positioned to cut the valve cusps, and then retracted. With proper orientation of the blades, it is unnecessary to make more than one pass with the valvulotome. As shown in FIG. 6, the head 14 and dilator 28 of the valvulotome, both being slightly larger than the internal diameter of the vein 40, expand the wall of the vein, thereby preventing the points of the blades 24 and 26 from catching on the branches or damaging the interior wall of the vein. Following destruction of the valves in the vein, anastomoses are performed to attach the vein to the femoral artery.

The valvulotome blade configuration produces highly reliable and effective destruction of venous valve cusps. The blade configuration, defined by intersecting conical and planar surfaces, as shown in FIGS. 4 and 5, can be produced easily with a high degree of accuracy and consistency.

Modifications can be made to the valvulotome described. For example, the outer blade-defining surface 32 can be tapered either toward the proximal end or toward the distal end of the instrument. The head 18 can be formed in various alternative shapes and sizes, and the rod can be provided in various dimensions. The handle 10 can take various alternative forms. For example, the milled flat on the handle can be in a plane perpendicular to a line between the blade tips, in which case the surgeon would maintain the flat in parallel relationship to the skin of the patient at a location adjacent to the location of the valvulotome head. The rod can be formed so that the portion extending between the head and the dilator is narrower than the portion extending between the handle and the dilator. Still other modifications can be made to the instrument described without departing from the invention as defined in the following claims.

I claim:

1. A valvulotome for cutting valve leaflets in a vein in order to make the vein usable as a by-pass vessel for an artery, comprising a thin, elongated rod having distal and proximal ends, said rod being capable of insertion into a vein, a head secured to the distal end of the rod, the head having a blunt tip and a proximal side, and having at least one sharp-pointed blade extending in the proximal direction from the proximal side of the tip, the point of the blade being located radially inwardly with respect to the outer surface of the tip, and the blade being defined by the following four surfaces, all intersecting substantially at the point of the blade:

(a) a first surface which is part of a first cone coaxial with a portion of said rod adjacent to the distal end thereof, said first cone being a right circular cone having its apex toward the distal end of the rod and having its base toward the proximal end of the rod;
   (b) a second surface which is part of a geometric surface selected from the group consisting of a right circular cylinder and a second right circular cone, said geometric surface being coaxial with said first cone and intersecting said first cone;
   (c) a third surface which is a part of a first plane; and
   (d) a fourth surface which is part of a second plane, said third and fourth surfaces extending substantially from the proximal side of the tip to the point of the blade and converging toward each other, proceeding in the proximal direction, and said first and second planes intersecting each other along a line of intersection which is substantially perpendicular to the axis of the rod adjacent to said distal end thereof.

2. A valvulotome according to claim 1 in which both of said first and second surfaces extend substantially from the proximal side of the tip to the point of the blade.

3. A valvulotome for cutting valve leaflets in a vein in order to make the vein usable as a by-pass vessel for an artery, comprising a thin, elongated rod having distal and proximal ends, said rod being capable of insertion into a vein, a head secured to the distal end of the rod, the head having a blunt tip and a proximal side, and having a pair of sharp-pointed blades located on opposite sides of the rod and extending in the proximal direction from the proximal side of the tip, the points of the blades being both located radially inwardly with respect to the outer surface of the tip, and each blade being defined by the following four surfaces, all intersecting substantially at the point of the blade:.
 (a) a first surface which is part of a first cone coaxial with a portion of said rod adjacent to the distal end thereof, said first cone being a right circular cone having its apex toward the distal end of the rod and having its base toward the proximal end of the rod;
 (b) a second surface which is part of a geometric surface selected from the group consisting of a right circular cylinder and a second right circular cone, said geometric surface being coaxial with said first cone and intersecting said first cone;
 (c) a third surface which is a part of a first plane; and
 (d) a fourth surface which is part of a second plane, said third and fourth surfaces extending substantially from the proximal side of the tip to the point of the blade and converging toward each other, proceeding in the proximal direction, and said first and second planes intersecting each other along a line of intersection which is substantially perpendicular to the axis of the rod adjacent to said distal end thereof.

4. A valvulotome according to claim 3 in which the first surface of each blade of said pair of blades is a part of the same right circular cone.

5. A valvulotome according to claim 3 in which the number of sharp-pointed blades on the blunt tip is two.

6. A valvulotome according to claim 3 in which the second surface of each blade of said pair of blades is a part of the same geometric surface selected from the group consisting of a right circular cylinder and a second right circular cone, said geometric surface being coaxial with said first cone and intersecting said first cone.

7. A valvulotome according to claim 3 in which the third surface of the each blade of said pair lies in the same plane as the third surface of the other blade of said pair.

8. A valvulotome according to claim 3 in which the third surface of the each blade of said pair lies in the same plane as the third surface of the other blade of said pair and the fourth surface of each blade of said pair lies in the same plane as the fourth surface of the other blade of said pair.

9. A valvulotome according to claim 3 in which the first surface of each blade of said pair of blades is a part of the same right circular cone, and the second surface of each blade of said pair of blades is a part of the same geometric surface selected from the group consisting of a right circular cylinder and a second right circular cone, said geometric surface being coaxial with said first cone and intersecting said first cone.

10. A valvulotome according to claim 3 in which:
 the first surface of each blade of said pair of blades is a part of the same right circular cone;
 the second surface of each blade of said pair of blades is a part of the same geometric surface selected from the group consisting of a right circular cylinder and a second right circular cone, said geometric surface being coaxial with said first cone and intersecting said first cone; and
 the third surface of the each blade of said pair lies in the same plane as the third surface of the other blade of said pair.

11. A valvulotome according to claim 3 in which:
 the first surface of each blade of said pair of blades is a part of the same right circular cone;
 the second surface of each blade of said pair of blades is a part of the same geometric surface selected from the group consisting of a right circular cylinder and a second right circular cone, said geometric surface being coaxial with said first cone and intersecting said first cone;
 the third surface of the each blade of said pair lies in the same plane as the third surface of the other blade of said pair; and
 the fourth surface of each blade of said pair lies in the same plane as the fourth surface of the other blade of said pair.

12. A valvulotome according to claim 3 in which:
 the first surface of each blade of said pair of blades is a part of the same right circular cone;
 the third surface of the each blade of said pair lies in the same plane as the third surface of the other blade of said pair; and
 the fourth surface of each blade of said pair lies in the same plane as the fourth surface of the other blade of said pair.

13. A valvulotome according to claim 3 in which:
 the second surface of each blade of said pair of blades is a part of the same geometric surface selected from the group consisting of a right circular cylinder and a second right circular cone, said geometric surface being coaxial with said first cone and intersecting said first cone;
 the third surface of the each blade of said pair lies in the same plane as the third surface of the other blade of said pair; and
 the fourth surface of each blade of said pair lies in the same plane as the fourth surface of the other blade of said pair.

14. A valvulotome according to claim 3 in which both of said first and second surfaces of each blade extend substantially from the proximal side of the tip to the point of the blade.

* * * * *